United States Patent
Danérol et al.

(10) Patent No.: US 11,701,447 B2
(45) Date of Patent: Jul. 18, 2023

(54) COMPOSITION HAVING EXCELLENT PERMEABILITY TO WATER VAPOUR

(71) Applicant: URGO RECHERCHE INNOVATION ET DEVELOPPEMENT, Chenove (FR)

(72) Inventors: Anne-Sophie Danérol, Dijon (FR); Christelle Guillamaud, Chenove (FR); Jean-Marc Pernot, Dijon (FR)

(73) Assignee: URGO RECHERCHE INNOVATION ET DEVELOPPEMENT, Chenove (FR)

( * ) Notice: Subject to any disclaimer, the term of this patent is extended or adjusted under 35 U.S.C. 154(b) by 347 days.

(21) Appl. No.: 16/768,295

(22) PCT Filed: Feb. 20, 2019

(86) PCT No.: PCT/HR2019/050386
§ 371 (c)(1),
(2) Date: May 29, 2020

(87) PCT Pub. No.: WO2019/162613
PCT Pub. Date: Aug. 29, 2019

(65) Prior Publication Data
US 2020/0289700 A1   Sep. 17, 2020

(30) Foreign Application Priority Data

Feb. 20, 2018   (FR) ..................... 18 51443

(51) Int. Cl.
*A61L 15/58*   (2006.01)
*A61L 15/44*   (2006.01)
*C09J 133/08*  (2006.01)

(52) U.S. Cl.
CPC ............. *A61L 15/585* (2013.01); *A61L 15/44* (2013.01); *C09J 133/08* (2013.01)

(58) Field of Classification Search
CPC ........ A61L 15/585; A61L 15/44; A61L 15/58; C09J 133/08; C09J 133/10; C09J 133/16; C09J 2433/00; C09J 2301/412; C08L 33/20
See application file for complete search history.

(56) References Cited

U.S. PATENT DOCUMENTS

| | | | |
|---|---|---|---|
| 5,164,444 A * | 11/1992 | Bernard | ................. C09J 133/08 526/318 |
| 5,623,011 A * | 4/1997 | Bernard | ................. C09J 133/08 524/270 |
| 6,080,797 A | 6/2000 | Nishida | |
| 6,429,265 B2 * | 8/2002 | Nishida | ................... A61L 15/60 525/367 |
| 2004/0241215 A1 * | 12/2004 | Lipman | ............... A61F 13/0246 424/445 |

FOREIGN PATENT DOCUMENTS

| WO | 2008/074333 A1 | 6/2008 |
|---|---|---|
| WO | 2015/192122 A1 | 12/2015 |

OTHER PUBLICATIONS

International Search Report dated May 13, 2019 in corresponding International Application No. PCT/FR2019/050386; 5 pages.

* cited by examiner

*Primary Examiner* — Scott R. Walshon
(74) *Attorney, Agent, or Firm* — Maier & Maier, PLLC

(57) ABSTRACT

A composition including a solution at least one acrylic adhesive and particles of a cross-linked polymer having a carboxylate-group density between 2.0 and 12.0 meq/g and an average pore size between 0.005 and 1.0 μm, usable in particular for creating an adhesive matrix suitable for any device, for example for medical aims such as a patch, a film, a strip or a dressing, preferably a dressing, or suitable for any device of the functional textile type such as a sports item.

12 Claims, 1 Drawing Sheet

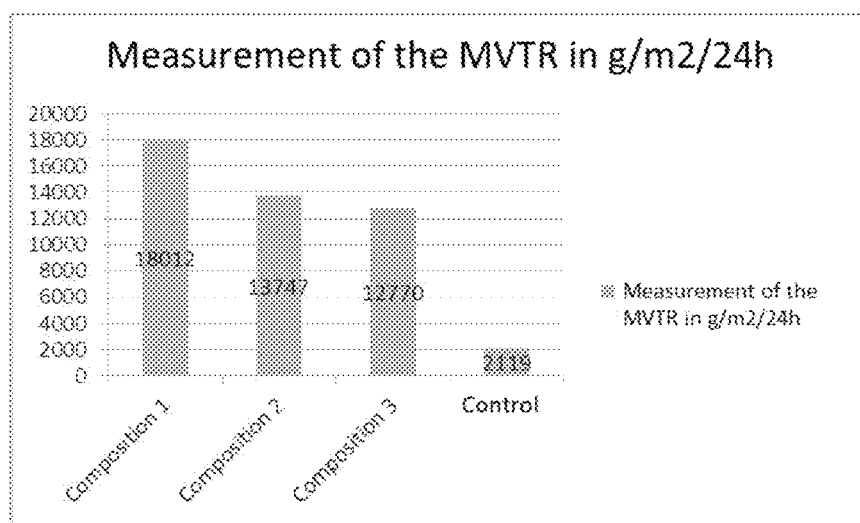

COMPOSITION HAVING EXCELLENT PERMEABILITY TO WATER VAPOUR

FIELD

The present invention relates particularly to a composition having excellent permeability to water vapour. This composition is in particular capable of implementing this excellent property in such varied technical fields as the medical field, agri-food packaging, motor vehicles, sports or leisure technical items or the textile field.

BACKGROUND

A dressing can be likened in particular to a protective device allowing to cover a wound. A dressing can have a plurality of other functions that can be combined with each other or not, such as:
- protecting the wound and insulating it from the outside environment;
- allowing better healing by maintaining a favourable humid environment on the bed of the wound;
- stopping negligible bleeding;
- bringing the edges of a wound closer together;
- absorbing and managing the exudates in order to preserve the edges of the wound and the perilesional skin.

The natural healing of a wound occurs in three successive phases, each of these phases being characterised by specific and different cellular activities: the cleaning phase, the granulation phase and the epithelialisation phase. Throughout the healing process, the wound produces fluid or viscous exudates that must if possible be absorbed by a healing dressing or evacuated by the latter to be guided towards a reservoir outside of the wound (case of negative-pressure therapy).

According to the seriousness of the wound, the healing process can last from several days to several months. In the case of particularly exudative wounds, the fluid or viscous exudates can flood the bed of the wound and form an environment favourable to the degradation of the perilesional healthy tissue, because of the maceration of the tissue or its superinfection.

For this type of wound, the role of a dressing is therefore to absorb or to manage these fluid exudates to limit the maceration, while remaining in contact with the wound throughout the healing process, in order to guarantee a protection of the wound with respect to the outside environment.

The creation of a dressing must thus comply with complex technical specifications and reconcile contradictory characteristics. In particular, the dressing must have good breathability while avoiding the risks of leaks and of maceration, be impermeable to liquids and to bacteria while being breathable (that is to say permeable to water vapour), retain its cohesion when it is removed, and be easy to manufacture. The dressing must also be easy to place and remain in place as long as possible over time without altering the perilesional skin, have a high capacity for absorption of the exudates, and not alter the healing of the wound during its removal. Finally, the dressing must be compatible with the complementary use of an immobilisation system.

To favour a part of the management of the fluids through the dressing, it is known to implement in the latter various layers that can in particular consist of polymer materials and having high permeability to water vapour (MVTR). Indeed it is estimated that over a day, the perspiration of the skin generates an imperceptible loss of water of approximately 250 g/m$^2$ [B. Gabard in the Encyclopédie médico-chirurgicale, 50-140-E-10]. Thus, to be considered to be effective, a medical device overall must thus have a permeability to water vapour (MVTR) higher than this value.

It is thus always sought to optimise the permeability to water vapour of each of the layers forming a dressing. In particular, the development of the breathability of the adhesive matrix (also called adhesive mass), generally forming a layer of intermediate contact with the skin, takes on a particular interest. Nevertheless, the improvement of the breathability of the adhesive matrix is generally accompanied by a very significant reduction in the adhesive power of said matrix on the skin. Indeed, to promote the permeability to water vapour, it is routine to perforate the matrix, which limits the contact surface of the latter with the skin, thus reducing its adhesive power.

The application WO 2008074333 from the company Coloplast describes improving the permeability of adhesive masses and describes an elastomer matrix for a medical device comprising a triblock elastomer of the S-I-S type and a water-soluble salt in order to increase the permeability to water vapour to levels of 20 g/m$^2$/24 h.

Nevertheless, compositions are still sought for adhesive matrices entering into the makeup of any device, and in particular any device for medical aims, which have improved properties of permeability to water vapour, while preserving sufficient adhesive power.

The present invention proposes a composition, in particular capable of being implemented in the form of an adhesive matrix, allowing to solve all of these issues, as well as a medical device implementing it.

SUMMARY

Thus, the present invention has allowed to develop a specific composition containing at least one acrylic adhesive and particles of a cross-linked polymer having a carboxylate-group density between 2.0 and 12.0 meq/g and an average pore size between 0.005 and 1.0 μm, allowing the preparation of an adhesive matrix capable of being implemented in a device, preferably a medical device such as a dressing, said matrix having a very good permeability to water vapour (MVTR), while preserving sufficient adhesive power (AP).

More precisely, it has been discovered, and this forms the foundation of the present invention, that by combining, in a composition, at least one acrylic adhesive with specific particles of a cross-linked polymer having a particular carboxylate-group density and a pore size that is also particular, it is possible, in a completely surprising manner, to optimise the diffusion of water vapour through the composition, in particular when the latter is implemented in the form of an adhesive matrix. The improvement of the properties of permeability to water vapour of the composition allows, when it is implemented in a medical device such as a dressing, to optimise the level of humidity at the skin, thus favouring better healing. Thus according to a first aspect, the object of the present invention is a composition, in particular useful for the manufacturing of dressings, comprising
- for 100 parts by weight of at least one acrylic adhesive,
- from 0.01 to 25 parts by weight of particles of a cross-linked polymer having a carboxylate-group density between 2.0 and 12.0 meq/g and an average pore size between 0.005 and 1.0 μm.

DETAILED DESCRIPTION OF THE FIGURE

FIG. 1 presents the results of the measurements of permeability to water vapour.

Adhesive Polymer

The composition according to the invention comprises at least one acrylic adhesive.

Preferably, the acrylic adhesive implemented in the compositions of the invention is physiologically acceptable for the skin, and its structure is at least partly cross-linked, preferably totally cross-linked.

The adhesives suitable for the present invention include the soft skin adhesives (SSA) and the pressure-sensitive adhesives (PSA).

According to a preferred embodiment of the invention, the acrylic adhesive is a pressure-sensitive adhesive (PSA).

According to a preferred embodiment of the invention, the acrylic adhesive is a polymer of acrylic adhesive implemented in the form of a solution, or in the form of a suspension. Preferably, the polymer of acrylic adhesive is implemented in the form of an aqueous suspension.

When the acrylic adhesive is introduced into the composition according to the invention in the form of a suspension, preferably in the form of an aqueous suspension, said suspension having between 40 and 80% acrylic adhesive polymer, relative to the total weight of the suspension.

According to a preferred embodiment, the polymer of pressure-sensitive acrylic adhesive is prepared from at least one monomer of alkyl acrylate.

The monomer of alkyl acrylate suitable for the creation of the acrylic adhesive according to the invention is in particular chosen from the following monomers: isooctyl acrylate, 2-ethylhexyl acrylate, butyl acrylate, sec-butyl acrylate, methyl butyl acrylate, 4-methyl 2-pentyl acrylate, vinyl acrylate and their derivatives.

In particular, the polymer of acrylic adhesive can contain from 30% to 98% by weight of at least one monomer of alkyl acrylate. For example, the total concentration of alkyl acrylate is between 60 and 85% by weight relative to the total weight of the monomer.

Comonomers can be used in the context of the present invention. These monomers include in a non-limiting way the unsaturated carboxylic or dicarboxylic acids such as methacrylic acid, acrylic acid, fumaric acid, dibutyl fumarate, dioctyl maleate and their derivatives.

Other comonomers can be used such as the methacrylates like methyl methacrylate, isodecyl methacrylate or other alternatives, the styrenes, vinyl pyrrolidone, and their derivatives.

The examples of commercially available pressure-sensitive acrylic adhesives include the adhesives marketed under the brand Gelva GME® by Cytec then Henkel, Aeroset® by Ashland, Novacryl® by Omnova, Flexcryl® by Air Products, Robond® by Dow, Duro-Tak® by Henkel, or Aquence® PS also by Henkel.

Preferably, the pressure-sensitive adhesive acrylic polymer used in the context of the present invention is that marketed under the product name Aquence® PS 6084-33 by the company HENKEL.

The composition according to the invention comprise 80 to 99.99% by weight, relative to the total weight of the composition, of at least one acrylic adhesive.

Particles of Cross-Linked Polymer

The compositions according to the invention comprise particles of a cross-linked polymer having a carboxylate-group density between 2.0 and 12.0 meq/g and an average pore size between 0.005 and 1.0 μm.

The "average size of the pores" designates an average size expressed in volume, the value of which can be calculated by the formula 4V/S where S is the specific surface area and V is the volume of pores per unit of mass obtained from a pore-size distribution measured by the mercury compression method.

The average size of the pores, expressed in volume, can be determined by any method known to a person skilled in the art, for example by mercury intrusion porosimetry or nitrogen adsorption sorptometry.

For example, the nitrogen adsorption sorptometry can be carried out via a Micromeritics TriStar II apparatus coupled with a Micromeritics Smart VacPrep. The batch to be characterised is for example subjected to a degassing phase for 24 hours at ambient temperature then 5 hours at 50° C. The temperature during the test is $-196°$ C., and the pressure is maintained in a range of $0<P/P_0<0.30$ with $P_0$=saturation vapour pressure of the nitrogen.

The mercury intrusion porosimetry can be implemented via a measurement cell for powder having a volume of 3 cm$^3$ and a capillary having a volume of 0.387 cm$^3$. The analysis is carried out in two steps: in a first step the "penetrometer-sample" assembly is in a "low pressure" configuration (measurement from 0.52 psia (primary vacuum) up to 30 psia or 2 bar); in a second step the "penetrometer-sample" assembly is in a "high pressure" configuration (measurement up to 6,000 psia or 4,000 bar). The minimum size of the accessible pores is 3 mm According to a preferred embodiment, the particles of cross-linked polymer implemented in the context of the present application have a specific surface area of less than 1 m$^2$/g. The specific surface area can in particular be measured by the physical adsorption BET method, well known to a person skilled in the art.

According to a preferred embodiment, the polymer implemented is an organic polymer.

The polymer implemented has a carboxylate-group density between 2.0 and 12.0 meq/g. The carboxylate group is a polar group conferring the desired properties of absorption of humidity onto the polymer.

There is no particular limitation as to the nature of the salt implemented for the formation of the carboxylate groups. This can for example be a salt of an alkali metal such as Li, Na, K, Rb and Cs, of an alkaline earth metal such as Be, Mg, Ca, Sr and Ba, of other metals such as Cu, Zn, Al, Mn, Ag, Fe, Co and Ni, NH4 and organic cations such as amines.

Preferably, the carboxylate salt used in the context of the present invention is sodium carboxylate.

The introduction of carboxylate groups can be carried out by any method known to a person skilled in the art. For example, a monomer carrying a carboxylate group can be homopolymerised or copolymerised with other monomers to give the polymer according to the invention. Alternatively, a polymer carrying carboxylate groups can be salified. Again alternatively, a polymer can first be grafted by carboxylate groups, which are then salified. These methods for introducing carboxylate groups are described in detail in the patent application U.S. Pat. No. 6,080,797 which is reused and incorporated by reference into the present application.

A typical example of particles of cross-linked polymer according to the invention can be created from acrylonitrile or methacrylic acid.

More particularly, microparticles of cross-linked polymer, in particular of polyacrylonitrile, according to the invention can be obtained by coagulation or by precipitation polymerisation to give an agglomerate of particles of polyacrylonitrile or a polymer of acrylonitrile, this agglomerate or this polymer undergoes a cross-linking with hydrazine or a derivative of hydrazine and finally an at least partial hydrolysis of the residual nitrile groups so as to obtain a carboxylate-group density between 2.0 and 12.0 meq/g. Moreover, the various steps of this method allow to obtain an average pore size between 0.005 and 1.0 µm.

For illustrative purposes, a first method allowing the manufacturing of a cross-linked polymer according to the invention involves preparing a solution of polymer from an acrylonitrile polymer and a solvent, then coagulating said solution in a solvent which is not a solvent for said acrylonitrile polymer to obtain a porous acrylonitrile polymer, then cross-linking said porous polyacrylonitrile with a hydrazine, said cross-linking being finally followed by a hydrolysis of the residual nitrile groups in such a way as to obtain a carboxylate-group density between 2.0 and 12.0 meq/g and an average pore size between 0.005 and 1.0 µm.

Alternatively, a second method allowing the manufacturing of a cross-linked polymer according to the invention involves precipitation polymerising a mixture of monomers containing at least 50% by weight of acrylonitrile to obtain a porous acrylonitrile polymer, then cross-linking of said porous polyacrylonitrile with a hydrazine and hydrolysis of the residual nitrile groups in such a way as to obtain a carboxylate-group density between 2.0 and 12.0 meq/g and an average pore size between 0.005 and 1.0 µm.

These methods are described more precisely in the patent application U.S. Pat. No. 6,080,797 which is reused and incorporated by reference into the present application.

Nevertheless, any particles having the required properties of carboxylate-group density or pore size are suitable for the creation of a composition according to the invention. A typical alternative would devote for example the creation of such particles from methacrylic acid as described in example 5 of the patent U.S. Pat. No. 6,080,797.

There is no particular limitation as to the shape of the particles of polymer implemented according to the invention.

In the sense of the present invention, the cross-linked polymer according to the invention is characterised by an equilibrium relative humidity (measured at 20° C. under at atmosphere at 65% relative humidity) between 20 and 80%, preferably between 30 and 70%.

According to a specific embodiment, the particles of cross-linked polymer according to the invention have an average size between 0.1 and 100 µm, preferably between 0.3 and 64 µm.

According to another specific embodiment, the particles of a cross-linked polymer according to the invention have an apparent density between 0.1 and 1 g/cm$^3$, preferably between 0.2 and 0.7 g/cm$^3$.

Such particles are for example marketed by the company Japan Exlan Co., Ltd under the name of Taftic® HU 707E, Taftic® HU 720SF or Taftic® HU 1200P.

They can be introduced into the compositions according to the invention in the form of powder, or in the form of particles in suspension or in dispersion in water.

The composition according to the invention comprises between 0.01 and 25 parts by weight, for 100 parts by weight of at least one acrylic adhesive, of a cross-linked polymer having a carboxylate-group density between 2.0 and 12.0 meq/g and an average pore size between 0.005 and 1.0 µm, preferably from 0.03 to 15 parts by weight.

Active Ingredients

Besides the particles of cross-linked polymer having a carboxylate-group density between 2.0 and 12.0 meq/g and an average pore size between 0.005 and 1.0 µm, the composition according to the invention can comprise one (or more) other active substance(s) allowing to induce or to accelerate healing or capable of playing a favourable role in skin treatment.

Among these active substances, mention can be made, in particular, as examples, of:

the agents promoting healing such as retinol, vitamin A, vitamin E, N-acetyl hydroxyproline, the extracts of Centella Asiatica, papain, the essential oils of thyme, niaouli, rosemary, sage, hyaluronic acid, potassium sucrose octasulphate, sucralfate, allantoin;

the antibacterial agents such as the salts or complexes of silver (like the sulphates of silver, the nitrates of silver, the sulphamides of silver or the zeolites containing silver), the salts of zinc or of copper, metronidazole, neomycin, the penicillins, clavulanic acid, the tetracyclines, minocycline, chlorotetracycline, the aminoglycosides, amikacin, gentamicin, the probiotics;

the antiseptics such as chlorhexidine, trichlosan, biguanide, hexamidine, thymol, Lugol's iodine, povidone-iodine, the chloride of benzalkonium and of benzethonium;

the analgesics such as paracetamol, codeine, dextropropoxyphene, tramadol, morphine and its derivatives, the corticoids and their derivatives;

the local anaesthetics such as lidocaine, benzocaine, dibucaine, pramoxine hydrochloride, bupivacaine, mepivacaine, prilocaine, etidocaine;

the anti-inflammatory drugs such as the nonsteroidal anti-inflammatory drugs (NSAIDs), aspirin or acetylsalicylic acid, ibuprofen, ketoprofen, flurbiprofen, diclofenac, aceclofenac, ketorolac, meloxicam, piroxicam, tenoxicam, naproxen, indomethacin, naproxcinod, nimesulide, celecoxib, etoricoxib, parecoxib, rofecoxib, valdecoxib, phenylbutazone, niflumic acid, mefenamic acid.

These active agents can be used in a quantity of approximately 0.01 to 25 parts by weight, preferably from 1 to 21 parts by weight, for 100 parts by weight of at least one acrylic adhesive.

Of course, the composition according to the invention can also comprise one or more other compounds known for their action in the cleaning phase for example such as:

enzymes;

urea.

Adhesive Matrix

In order to create any device, and preferably a dressing, the compositions according to the invention are preferably shaped by coating then drying, to form an adhesive matrix.

The object of the invention, according to another aspect, is thus an adhesive matrix obtained from a composition according to the invention as described above.

This matrix can be continuous, that is to say solid and not having the slightest perforation, or discontinuous, that is to say having at least one perforation or through-holes; preferably, said adhesive matrix is continuous.

In the presence of through-holes, the latter can be created by perforation, hollowing or punching of a composition according to the invention previously formed into a thin layer, alone or combined with a temporary support.

The through-holes can have any given geometry and have for example a circular, rectangular, trapezoidal or square transverse cross-section.

These holes are distributed, preferably regularly, with a density such that the total surface area of the holes represents between 20 and 70% and preferably between 30 and 60% of the total surface of the matrix.

In general, the adhesive matrices according to the invention have a thickness between 0.1 µm and 2 mm, and preferably between 5 µm and 150 µm.

It is also possible to use this adhesive matrix to coat a frame or a support.

Device

The object of the invention, according to a preferred embodiment, is therefore a medical device such as a patch, a film, a strip or a dressing, or a device of the functional textile type such as a sports item, comprising an adhesive matrix as described above. Preferably, said device is a dressing characterised in that it comprises an adhesive matrix as described above.

According to a preferred embodiment, the present application aims to cover a dressing comprising an adhesive matrix in the form of a thin layer obtained from a composition comprising:

for 100 parts by weight of at least one acrylic adhesive, from 0.01 to 25 parts by weight of particles of a cross-linked polymer having a carboxylate-group density between 2.0 and 12.0 meq/g and an average pore size between 0.005 and 1.0 µm.

The adhesive matrix can be used alone to form the device or in combination with one or more layers, such as foams, textiles, composite materials or films.

The adhesive matrix can be at any level of the device, that is to say form any one of the various layers of the device, and can be in contact with the skin, the wound.

The present invention is illustrated in the non-limiting examples presented below.

EXAMPLE

Preparation of the Compositions

The compositions 1 to 3 were made using the following components in the proportions, expressed in parts by weight, mentioned in table 1 below.

Manufacturing of the Composition

In a stirred mixing device, a determined quantity of particles of Taftic HU in the form of powder or in an aqueous suspension are added to a suspension of an Aquence PS 6084-33 base until a homogenous mixture is obtained.

Acrylic Adhesive:
Aquence PS 6084-33 from Henkel
Particles of Cross-Linked Polymer:
Taftic HU-720SF from the company Japan Exlan Co., Ltd
Taftic HU-1200P from the company Japan Exlan Co., Ltd
Taftic HU-707E from the company Japan Exlan Co., Ltd

TABLE 1

|  | Compo. 1 | Compo. 2 | Compo. 3 | Control |
|---|---|---|---|---|
| Taftic HU-720 SF from Japan Exlan Co., Ltd | 4.16 | | | |
| Taftic HU-1200 P from Japan Exlan Co., Ltd | | 4.16 | | |
| Taftic HU-707 E from Japan Exlan Co., Ltd | | | 20.48 | |
| Aquence PS 6084-33 from Henkel | 100 | 100 | 100 | 100 |

Measurement of the permeability to water vapour:

The conditions for carrying out the test are based on the standard NF EN 13726—liquids in contact.

Equipment/Instruments
Scale resolution 0.1 mg
Hollow punch diameter 44 mm
Measurement cell made of aluminium having a diameter D=35.7 mm and surface area 10 cm$^2$
Volumetric flask (=25 mL) or metering pump
Thermostatically controlled air oven at 37° C. and <20% relative humidity (RH)
Air-conditioned room at 21° C.+/−2−RH at 60%+/−15
Reactants: demineralised water and NaCl, CaCl2 solution
Sampling/Conditioning of the Samples
Number of test specimens n≥5
Temperature T=37° C.±2° C.
Hygrometry RH<20%

Operating Mode

The conditions for carrying out the test are based on the standard NF EN 13726—liquids in contact, are the following.

The principle of this measurement is the following:
1. Pour a volume V of liquid into the cell.
2. Position, on the opening of the measurement cell, the sample to be tested (adhesive face on the siliconised joint if adhesive is applied to the product).
3. Position above the sample, centred to avoid leaks, the maintaining device then screw the 3 screws until stopped.
4. Weigh the assembly PMVTR$_0$.
5. Turn over the cells to place the liquid in contact with the sample. Place this assembly in an oven at a temperature T for a time t (t expressed in hours).
6. Weigh within 5 minutes of the end of the test (t) the entire device PMVTR1.

Expression of the Results

Calculate the water vapour transmission rate (MVTR)

$$MVTR_1 = (PMVTR_0 - PMVTR_1)/(\pi D^2/4)$$

$$MVTR_1 = 4(PMVTR_0 - PMVTR_1)/\pi D^2$$

Or, under the standard conditions, $MVTR_1 = (PMVTR_0 - PMVTR_1)/(10*10^{-4})$

Express the result in g/m$^2$/24 h.

Calculate the average of the n tests, give or take one g/m$^2$.

The results of the measurements of permeability to water vapour are presented in FIG. 1 and in table 2 below. These results show that each of the three compositions comprising particles of a cross-linked polymer according to the invention have a capacity for absorbing water vapour significantly greater than the control composition.

TABLE 2

|  | Values for MVTR in g/m$^2$/24 h |
|---|---|
| Composition 1 | 18,012 +/− 538 |
| Composition 2 | 13,747 +/− 3,265 |
| Composition 3 | 12,770 +/− 3,061 |
| Control | 2,119 +/− 741 |

Measurement of the Adhesive Power at 90°

The first step involves placing one of the compositions of the example onto a support of the nonwoven type and then cutting out a test specimen that is to say a strip of one of these combinations 20 mm wide and 300 mm long.

In a second step, the test specimen is applied, with a slight pressure of the finger on the steel plate in parallel to its largest dimension, without stretching the strip and while avoiding including the slightest air bubble.

Two there-and-back movements are carried out using an applicator roll, at a speed V1=10 mm/s and a weight P=2 kg/cm, without additional pressure, to obtain close contact between the acrylic adhesive and the steel plate.

The assembly is left to climatise at a temperature of 23+/−2° C. for a time t=10 min.

Finally, in a final step, the average force F of the peeling at 90° carried out at a speed V2=300 mm/min of the test specimen on the steel plate is recorded via an electronic dynamometer.

|  | Adhesive power at 90° on a steel plate (cN/cm) |
| --- | --- |
| Composition 1 | 278 +/− 35 |
| Control | 286 +/− 22 |

Therefore, the addition of particles of a cross-linked polymer having a carboxylate-group density between 2.0 and 12.0 meq/g and an average pore size between 0.005 and 1.0 µm thus allows to significantly increase the capacity for absorbing water vapour of the compositions according to the invention, without altering their adhesive power.

The invention claimed is:

1. A composition comprising:
   for 100 parts by weight of at least one acrylic adhesive,
   from 0.01 to 25 parts by weight of particles of a cross-linked polymer having a carboxylate-group density between 2.0 and 12.0 meq/g and an average pore size between 0.005 and 1.0 µm, and
   the particles of the cross-linked polymer have a specific surface area of less than 1 m²/g.

2. The composition according to claim 1, wherein the acrylic adhesive is in the form of a solution or a suspension.

3. The composition according to claim 2, wherein said suspension has between 40 and 80% of acrylic adhesive polymer, relative to the total weight of the suspension.

4. The composition according to claim 1, wherein the adhesive acrylic polymer is prepared from at least one monomer of alkyl acrylate selected from the group consisting of isooctyl acrylate, 2-ethylhexyl acrylate, butyl acrylate, sec-butyl acrylate, methyl butyl acrylate, 4-methyl 2-pentyl acrylate, or vinyl acrylate.

5. The composition according to claim 1, wherein the particles of cross-linked polymer are in the form of a powder, a dispersion or a suspension.

6. The composition according to claim 1, wherein the particles of cross-linked polymer have an average size between 0.1 and 100 µm.

7. The composition according to claim 1, wherein the cross-linked polymer is prepared from acrylonitrile or methacrylic acid.

8. The composition according to claim 1, wherein the composition comprises one or more active substance(s) allowing to induce or to accelerate healing or capable of playing a favourable role in skin treatment.

9. An adhesive matrix, wherein the adhesive matrix is obtained from the composition according to claim 1 by coating and drying.

10. A medical device, comprising the adhesive matrix according to claim 9.

11. The medical device according to claim 10, wherein the medical device is a dressing.

12. The composition according to claim 1, wherein the composition has a value of permeability to water vapor (MVTR) that is between 9,709 and 18,550 g/m²/24 h.

* * * * *